US00PP28163P3

(12) United States Plant Patent
Egger

(10) Patent No.: US PP28,163 P3
(45) Date of Patent: Jul. 4, 2017

(54) **'*PENSTEMON*' PLANT NAMED 'CHA CHA CHERRY'**

(50) Latin Name: ***Penstemon* hybrid**
Varietal Denomination: Cha Cha Cherry

(71) Applicant: Terra Nova Nurseries, Inc., Canby, OR (US)

(72) Inventor: Janet N. Egger, Wilsonville, OR (US)

(73) Assignee: Terra Nova Nurseries, Inc, Canby, OR (US)

( * ) Notice: Subject to any disclaimer, the term of this patent is extended or adjusted under 35 U.S.C. 154(b) by 259 days.

(21) Appl. No.: 14/545,243

(22) Filed: Apr. 13, 2015

(65) Prior Publication Data

US 2016/0302348 P1 Oct. 13, 2016

(51) Int. Cl.
*A01H 5/02* (2006.01)

(52) U.S. Cl.
USPC ..... Plt./465

(58) Field of Classification Search
USPC ..... Plt./465
CPC ..... A01H 5/02
See application file for complete search history.

(56) References Cited

PUBLICATIONS http://serenityinthegarden.blogspot.com/2015/02/cha-cha-cherry-penstemon-ooohhhh.html; Feb. 18, 2015; 18 pages.*

* cited by examiner

*Primary Examiner* — Kent L Bell
(74) *Attorney, Agent, or Firm* — Klarquist Sparkman, LLP

(57) ABSTRACT

A new and distinct cultivar of *Penstemon* plant characterized by medium size red flowers in dense clusters, long bloom time, attractive deep purple seed heads, a compact, upright, well branched habit, with multiple crown from the base, clean-looking, deep green, attractive foliage, and excellent vigor.

2 Drawing Sheets

Botanical denomination: *Penstemon* hybrid.
Variety designation: 'Cha Cha Cherry'.

BACKGROUND OF THE INVENTION

The present invention relates to a new and distinct cultivar of *Penstemon*, given the name, 'Cha Cha Cherry'. *Penstemon* is in the family Plantaginaceae (formerly Scrophulariaceae). This plant originated in a controlled breeding plan to create a compact, upright, medium size, multiflowered series. The exact parents are unknown, unnamed proprietary plants. This cultivar was selected for its compact growing habit, medium size flowers in dense clusters, long flowering time, vigor, and clean attractive look. It is an ideal plant for a sunny border in full sun.

Compared to plants of *Penstemon* Arabesque™ Red hybrid, an unpatented seed strain, the new cultivar is more vigorous, flowers earlier, and has more numerous flowers with no white eye rather than a white eye.

Compared to *Penstemon* 'Garnet', an unpatented plant, the new cultivar has an upright habit rather than somewhat floppy, larger, more numerous flowers that are red rather than rose red, and larger leaves.

*Penstemon* 'Cha Cha Cherry' is uniquely distinguished by its:

1. medium size red flowers in large dense clusters,
2. long bloom time,
3. compact, upright, well branched habit, with multiple crowns from the base, 4. attractive deep purple seed heads,
5. clean-looking, deep green, attractive foliage, and
6. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the habit of a group of sixteen-month-old plants the trial field in bud in mid-July in Canby, Oreg.

FIG. 2 shows one plant in a two gallon container from the same group in bloom in August.

DETAILED PLANT DESCRIPTION

Figure 3:
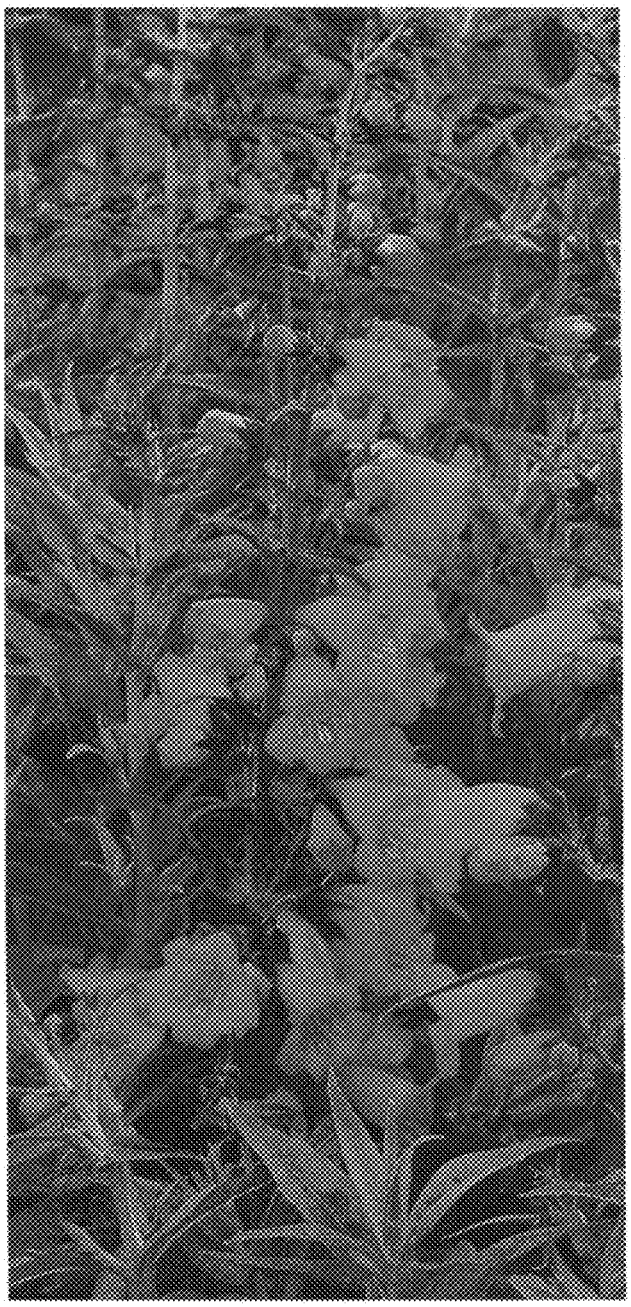
FIG. 3 shows a close up of the inflorescence.

The following is a detailed description of the new *Penstemon* cultivar based on observations of nine-month-old specimens grown outside in the trial field in full sun in Canby, Oreg. in August. The color descriptions are all based on *The Royal Horticultural Society Colour Chart,* 5$^{th}$ edition, 2007.

Plant:

*Type*.—Herbaceous perennial.

*Form*.—Upright, branching.

*Cold hardiness*.—USDA Zone 7-10.

*Size*.—Grows to 55 cm wide and 70 cm high to top of inflorescence.

*Vigor*.—Excellent.

*Stem number*.—About 12 main stems from the crown.

*Stem*.—Upright, 16 cm to 49 cm long and 6 mm to 10 mm wide (at the base), glabrous at base to glandular pubescent toward rachis, internodes grow to 4 cm long, Yellow Green 146C.

*Rooting*.—Roots easily from stem cuttings.

Leaf:

*Type*.—Simple.

*Arrangement*.—Opposite.

*Shape*.—Lanceolate.

*Venation*.—Pinnate, main vein on top Yellow Green 145B, bottom side Yellow Green 145C.

*Margins*.—Serrulate.

*Apex*.—Acuminate.

*Base*.—Attenuate.

*Blade size*.—Grows to 14 cm long and 3.6 cm wide.

*Surface texture*.—Glabrous on both sides.

*Petiole*.—None, sessile.

*Leaf color*.—Topside Green N137C, bottom side closest to Greyed Green 189A.

Inflorescence:

*Type*.—Terminal, many flowered, dense thyrse.

*Number of flowers per inflorescence*.—33 to 110.

*Size of inflorescence*.—Grows to 37 cm long and 8.6 cm wide.

*Peduncle*.—Grows to 2 cm long and 2.5 mm wide, sparsely pubescent, Yellow Green 146C where shaded and tinted Greyed Purple 187B where in sun.

*Rachis*.—9 to 31 cm long and 4 mm wide, sparsely pubescent, Yellow Green 146C where shaded and tinted Greyed Purple 187B where in sun.

*Pedicels*.—Grows to 5 mm long and 1 mm wide, pubescent, Yellow Green 146C in shade and lightly tinted Greyed Purple 187B where in sun.

*Bloom period*.—Mid June to frost in October in Canby, Oreg. if spent flowers are removed.

Flower bud:

*Size*.—2.3 cm long and to 10 mm wide.

*Description*.—Closed tubular, bulging, flattened ventrically.

*Color*.—Red 54B with lobe end 53A.

Flower:

*Type*.—Zygomorphic, perfect.

*Shape*.—Tubular, bilabiate.

*Size*.—Grows to 3.5 cm long and 2.7 cm wide.

*Corolla description*.—Grows to 3.5 cm long and 2.7 cm wide; tube is bulbous in the calyx for 5 mm long and 4 mm wide, narrowing then widening for 23 mm and flaring to 12 mm wide, 5 lobes, the two smaller top lobes flare back (each 9 mm wide and to 10 mm deep) and two larger lateral lobes curl back slightly (10 mm wide and 10 mm deep), and the lower lobe flares curls back slightly (10 mm wide and 10 mm deep), lower lobes overlap slightly, lobe margins entire, tips acute; outside glandular pubescent, inside sparsely pubescent; outside color Red 53B, inside color lobes Red 53B with edges Greyed Purple 187B, tube White N155B with bee tracks Greyed Purple 187B.

*Calyx description*.—9 mm deep and 10 mm wide, 5 overlapping lobes cut to the base, each lobe ovate in shape, 8 mm long and 4 mm wide, margins entire, tip acuminate, base cuneate, outside Yellow Green 146C tinted Greyed Purple 187A where in sun and on margins, inside Yellow Green 146C, glabrous inside and glandular pubescent outside.

*Pistil description*.—1, 26 mm long, ovary 4 mm long and 2 mm wide, Yellow Green 146D; style 20.5 mm long and less than 1 mm wide, style White N155B, stigma White NN155C.

*Stamen description*.—5, one sterile without an anther, held within the corolla 20 mm long, filaments 20 mm long and White N155B, anthers 2 mm long, Purple N77C, pollen White NN155C.

*Fragrance*.—None.

*Lastingness*.—A flower lasts 5 to 6 days.

Fruit:

*Type*.—Capsule.

*Fertility*.—Fair.

*Size*.—11 mm deep and 11 mm wide.

*Shape*.—Conical.

*Color*.—Purple N77A.

Seed:

*Shape*.—Irregular.

*Size*.—2 mm long.

*Color*.—Brown 200A.

Pests and diseases: The new cultivar is typical to the genus. No problems have been found in Canby, Oreg.

I claim:

1. A new and distinct cultivar of *Penstemon* plant substantially as illustrated and described.

* * * * *

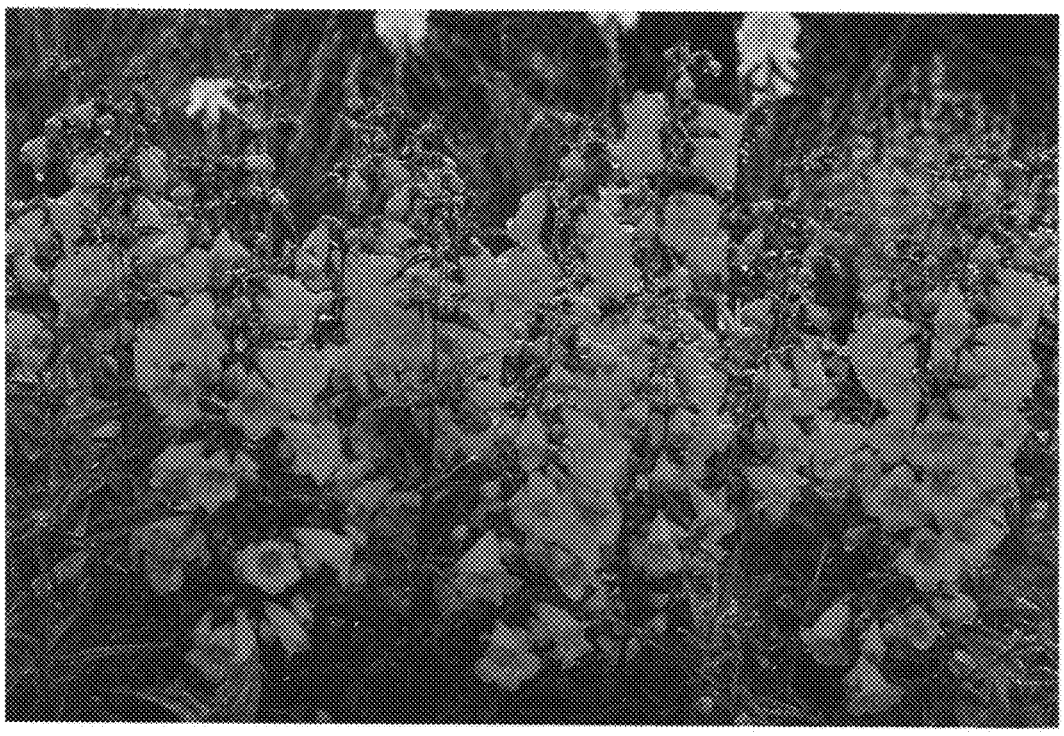

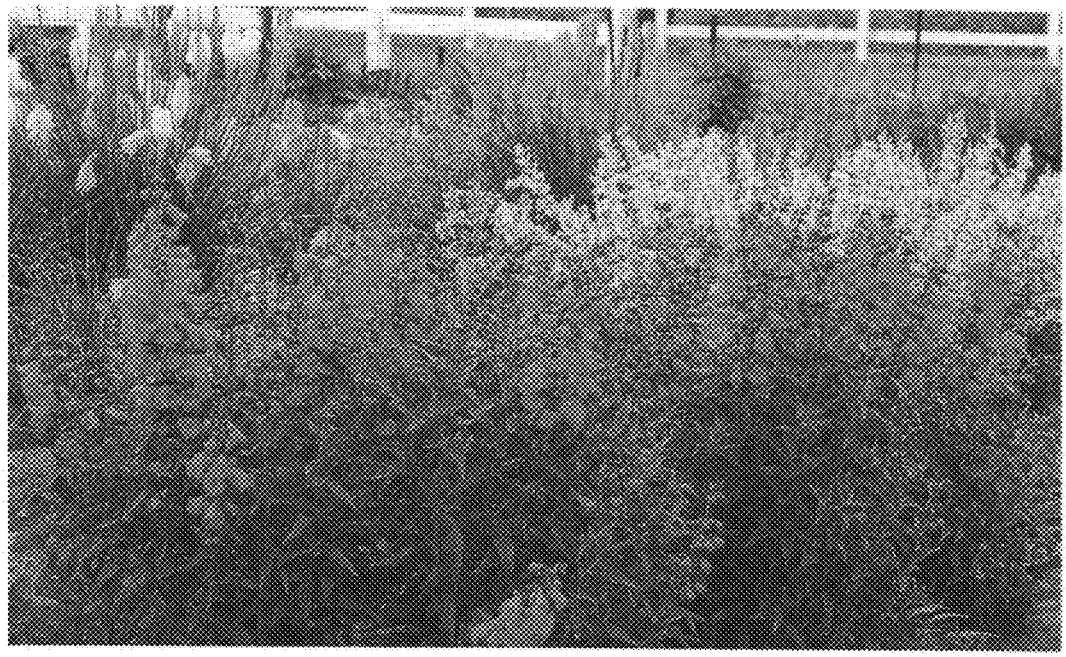
FIG. 1 above, FIG. 2 below